United States Patent [19]

Siedel et al.

[11] Patent Number: 5,156,947

[45] Date of Patent: Oct. 20, 1992

[54] PROCESS FOR REDUCTION OF THE MATRIX EFFECT IN A FRUCTOSAMINE DETERMINATION ASSAY

[75] Inventors: Joachim Siedel, Bernried; Joachim Ziegenhorn, Starnberg; Lieselotte Schellong, Munich; Bernd Vogt, Tutzing, all of Fed. Rep. of Germany

[73] Assignee: Boehringer Mannheim GmbH, Mannheim, Fed. Rep. of Germany

[21] Appl. No.: 64,336

[22] Filed: Jun. 19, 1987

[30] Foreign Application Priority Data

Jun. 21, 1986 [DE] Fed. Rep. of Germany ....... 3620817

[51] Int. Cl.$^5$ .......................... C12Q 1/00; C12Q 1/28; C12Q 1/30
[52] U.S. Cl. .......................................... 435/4; 435/10; 435/27; 435/28; 436/87; 436/88; 436/95; 436/175; 436/825; 436/904
[58] Field of Search .................. 436/34, 63, 67, 87, 436/88, 95, 111, 164, 175, 177, 178, 903, 904, 825; 435/4, 10, 25, 27, 28

[56] References Cited

U.S. PATENT DOCUMENTS

| | | | |
|---|---|---|---|
| 4,166,763 | 9/1979 | Esders et al. | 435/805 X |
| 4,168,205 | 9/1979 | Danninger et al. | 435/28 X |
| 4,455,371 | 6/1984 | Richardson et al. | 435/28 X |
| 4,563,422 | 1/1986 | Deneke et al. | 435/27 |
| 4,610,963 | 9/1986 | Matsui et al. | 435/25 X |
| 4,642,295 | 2/1987 | Baker | 436/87 |
| 5,002,893 | 3/1991 | Rosenthal | 436/87 |

FOREIGN PATENT DOCUMENTS

| | | |
|---|---|---|
| 0004857 | 10/1979 | European Pat. Off. . |
| 0014898 | 9/1980 | European Pat. Off. . |
| 0016962 | 10/1980 | European Pat. Off. . |
| 0148950 | 7/1985 | European Pat. Off. . |
| 0158964 | 10/1985 | European Pat. Off. . |
| 0215170 | 3/1987 | European Pat. Off. . |
| 2910737 | 10/1980 | Fed. Rep. of Germany . |
| 2084726 | 4/1982 | United Kingdom . |

OTHER PUBLICATIONS

Schleicher, et al., J. Clin. Chem. Clin. Biochem. 19: 81–87 (1981).
Seng, et al. J. Clin. Chem. 32: 560 (1986).
Hindle, et al., Ann. Clin. Biochem. 22: 84–89 (1985).
Chemical Abstracts, vol. 88, 1978, p. 226.
Johnson et al, Clin. Chim. Acta, vol. 127, pp. 87–95, 1982.

Primary Examiner—Robert J. Hill, Jr.
Attorney, Agent, or Firm—Felfe & Lynch

[57] ABSTRACT

This invention teaches a process for reducing protein matrix effects in assays for serum fructosamine. Blood or blood derived samples are used, and one adds two reagents, one of which reduces interference caused by non-specific reducing substances, the other of which eliminates turbidity. Incubation follows, and then the pH of the sample is adjusted and color forming reagent is added. In one embodiment, the incubation time is only 1–15 minutes. In another embodiment, the first reagent contains peroxidase.

31 Claims, 6 Drawing Sheets

NUMBER OF VALUE PAIRS : 20
CORRELATION COEFFICIENT : .985
REGRESSION OF Y FROM X : Y= .320+ .000295*X
REGRESSION OF X FROM Y : Y= .296+ .000304*X
STANDARD PRINCIPAL
 COMPONENT ANALYSIS : Y= .308+ .000300*X  —–—–—

× NORMAL SERUM          ⊙ DIABETIC SERUM

FIG. 5b

NUMBER OF VALUE PAIRS : 20
CORRELATION COEFFICIENT : .980
REGRESSION OF Y FROM X : Y= .282+ .000267*X
REGRESSION OF X FROM Y : Y= .254+ .000278*X
STANDARD PRINCIPAL
 COMPONENT ANALYSIS : Y= .268+ .000272*X  —·—·—·—

× NORMAL SERUM         ○ DIABETIC SERUM

FIG. 5c

NUMBER OF VALUE PAIRS : 20
CORRELATION COEFFICIENT : .978
REGRESSION OF Y FROM X : Y= .321+ .000297*X
REGRESSION OF X FROM Y : Y= .285+ .000311*X
STANDARD PRINCIPAL
  COMPONENT ANALYSIS  : Y= .303+ .000304*X  — · — · —

× NORMAL SERUM                    ⊙ DIABETIC SERUM

FIG. 5d

NUMBER OF VALUE PAIRS       : 20
CORRELATION COEFFICIENT : .977
REGRESSION OF Y FROM X   : Y= .567+ .000291*X
REGRESSION OF X FROM Y   : Y= .200+ .000305*X
STANDARD PRINCIPAL
  COMPONENT ANALYSIS        : Y= .385+ .000298*X    —·—·—·—

× NORMAL SERUM                              ⊙ DIABETIC SERUM

PROCESS FOR REDUCTION OF THE MATRIX EFFECT IN A FRUCTOSAMINE DETERMINATION ASSAY

The present invention is concerned with a process for the specific determination of the serum fructosamine content in blood or samples derived from blood in which disturbing sample components are removed before measurement of the fructosamine content.

By serum fructosamine content, there is to be understood the totality of non-enzymatic glycosilated serum proteins. These arise in that serum glucose forms Schiff bases via its carbonyl group with free protein amino residues. These subsequently pass over, by Amadori rearrangement, into fructosamines with stable ketomaine bonding. The reaction mechanism was investigated in detail, for example, by E. Schleicher and O. H. Wieland in J. Clin. Chem. Clin. Biochem., 19, 81–87/1981.

Because of the stability of the ketoamine bonding, the half life time of the serum fructosamine is practically identical with that of the serum proteins, the half life time of which is, on average, about 21 days. Corresponding investigations were published by L. Y. Seng and M. J. Staley in J. Clin. Chem., 32, 560/1986.

The extent of the fructosamine formation is proportional to the blood glucose level. As is known, in the case of diabetics, especially in the case of insufficient dietetic and medicamentary metabolic adjustment, this can be subject to considerable variations, involved with marked pathological phenomena.

The blood glucose determination only gives the physician information about the metabolic state at the time of the blood sampling. On the other hand, a longterm control over the metabolic state of the last 120 days is possible with the determination of the glycosylated haemoglobin ($HbA_1$). Because of its half life time, measurement of serum fructosamine is especially suitable for determining the success of metabolic control of diabetics by diet and therapeutical treatment over an average time of about 3 weeks. In conjunction with the established clinical diagnostic parameters of blood glucose, as well as of glycosylated haemoglobin ($HbA_1$), with a dependable, specific and practical method for serum fructosamine determination, the diagnostic arsenal for the supervision of diabetics can be widened by a valuable middle term parameter.

A process for the determination of serum fructosamine which, in principle, is simple to carry out, was described by U.S. Pat. No. 4,642,295 and by Johnson et al. in Clin. Chim. Acta, 127, 87–95/1982. It depends upon the fact that the ketoamine formed passed over in aqueous, alkaline medium into an enol form which acts reducingly on tetrazolium salts, for example nitrotetrazolium blue, and thereby provides a formazane coloured material. The extent of the coloured material formation measured photometrically in a definite time interval at 37° C. is proportional to the amount of fructosamine present.

In the case of the use of serum as sample material, this test is subject to disturbance since natural serum components, such as bilirubin and uric acid, also act reductively on tetrazolium salts. Also medicaments, for example α-methyldopa, medicament metabolic products, for example gentisic acid, which is a metabolite of acetylsalicylic acid, as well as ascorbic acid, lead, depending upon the concentration in the serum, to falsified measurement results.

Hitherto, serum fructosamine determinations also suffered from disturbances which are due to the total protein content varying from sample to sample. They lead to measurement value variations and thereby reduce the sensitivity of the determination process. These disturbances are known as matrix effects. This effect makes itself especially noticeable in the case of the addition of further protein, such as is usually the case, for example, in the production of standard solutions. Increasing amounts of protein slow down the reaction between fructosamine and color reagent (see E. J. Hindle et al., Ann. Clin. Biochem., 22, p. 84–89/1985).

Further difficulties arise in the case of the fructosamine determination in hyperlipaemic sera. In general, in order also to be able to obtain a sufficiently large measurement signal in the case of low fructosamine concentrations in the sample, a sample/reagent volume ratio of 0.1 is necessary. However, in the case of excessive triglyceride concentrations and in the case of such high proportions of sample, the resulting turbidity has a negative effect in the case of photometric measurement. The fructosamine determination becomes considerably more difficult or is even impossible.

Thus, there is still a need for a process for the specific determination of the serum fructosamine content in blood or in samples obtained from blood which does not suffer from the above-mentioned disadvantages. It is an object of the present invention to provide such a process.

Thus, according to the present invention, there is provided a process for the specific determination of the serum fructosamine content in blood or in samples derived from blood by reaction with an appropriate colour reagent and measurement of the colour change thereby brought about, wherein, before the colour reaction, non-specific reducing-acting and/or turbidity-causing sample components are removed at approximately neutral pH value, subsequently the pH is adjusted to a value of from about 10 to about 12 and the colour reagent is added thereto.

For the removal of non-specific reducing-acting sample components, the sample is mixed with one or more enzymatic or/and non-enzymatic oxidizing agents. As enzymatic oxidizing agents bilirubin oxidase, ascorbate oxidase or/and uricase and as non-enzymatic oxidizing agents hypochlorite or a hypochlorite generating compounds are advantageous. Especially advantageous as hypochlorite producing compound is N-chloro-p-toluenesulfonamide (chloramine T). That compound in contact with water slowly generates hypochlorous acid. That is a potent oxidizing agent in acidic and neutral but not in alkaline solution. It has proved to be especially advantageous when additionally peroxidase and/or catalase are added.

Surprisingly, we have ascertained that, by the addition of such one or more enzymatic or/and non-enzymatic oxidizing agents to the sample to be determined, disturbances due to all disturbing reducing-acting components are removed, i.e. the above-mentioned oxidizing agents oxidise not only bilirubin, uric acid or ascorbic acid, but they also remove disturbances due to other reducing-acting materials, for example medicaments, as well as metabolic products thereof. In the presence of one or more oxidizing agents, these substances are eliminated in the therapeutic concentration range or their concentration is lowered to an extent which no longer has any effect on the analysis. Peroxidase optionally present can, with possibly formed hydrogen peroxide, bring about additional oxidative breakdown processes, which additionally further increases the effectiveness of the oxidizing agent. Catalase optionally added serves, in particular, for the removal of excess hydrogen peroxide. By the addition of an appropriate detergent, preferably of a cationic detergent, for example oxyethylalkylammoniumphosphate (for example Dehyquart ®SP of the firm Henkel) surprisingly the oxidizing effect can be elevated. Especially potent is a mixture of enzymatic or/and non-enzymatic oxidizing agents, if it comprises chloramine T and additionally a cationic detergent, for example oxyethylalkylammoniumphosphate (for example Dehyquart ®SP of the firm Henkel). The concentration of the cationic detergent ranges from about 0.5 to about 4% by volume. As preferred range of concentration for Dehyquart ®SP has been determined about 1 to about 2% by volume.

Especially for the investigation of lipaemic samples, it has proved to be expedient optionally to add lipase to the oxidizing agent, optionally together with one or more detergents and/or salts of mineral acids. With the help of such a mixture, it is possible to eliminate turbidity-causing materials to such an extent that the subsequent colour measurement is no longer impaired.

Surprisingly, with the help of the above-mentioned substances for the removal of disturbing components, the measurement value variations due to varying total amounts of protein in the sample, known as the matrix effect, are also suppressed or completely removed.

For the removal of non-specific reducing-acting and/or turbidity-causing sample components, it has proved to be expedient to incubate the sample with a solution which contains one or more oxidising agents, as well as optionally one or more detergents and/or salts of mineral acids in an appropriate non-reducing buffer. For the preparation of this solution, there can be used all buffer substances which themselves do not act reducingly and the buffer action of which lies at approximately the neutral pH value. A pH range of about pH 6 to about pH 9 has proved to be advantageous, preferably a pH of about 7 to about 8.5 and especially preferably a pH of about 7.5 to about 8.0. The buffer concentration is normally about 10 to about 100 mmole/liter and especially preferably about 20 to about 70 mmole/liter. Aqueous potassium phosphate buffer has proved to be especially advantageous.

The concentration of the added enzymes depends upon the concentration of the disturbing compounds to be removed. Usually, these enzyme concentrations are from 0.01 to 10000 U/ml. Preferred concentration ranges are, for example, for

| uricase | 1-15 U/ml |
| bilirubin oxidase | 0.05-5 U/ml |
| ascorbate oxidase | 2-20 U/ml |
| lipase | 0.5-5 U/ml |
| peroxidase | 0.5-5 U/ml |
| catalase | 100-10000 U/ml |

Especially preferred concentration ranges of these enzymes are for

| uricase | 2-10 U/ml |
| bilirubin oxidase | 0.1-1 U/ml |
| ascorbate oxidase | 5-15 U/ml |
| lipase | 1-3 U/ml |
| peroxidase | 1-3 U/ml |
| catalase | 500-2000 U/ml. |

The concentration of the added hypochlorite or the hypochlorite generating compound depends upon the concentration of the disturbing compounds to be removed, too. Usually, hypochlorite or the hypochlorite generating compound is used in concentration ranges from about 50 to about 600 µmol/l, preferably from about 150 to about 300 µmol/l.

Detergents can be cationic, anionic or non-ionic. As anionic detergents, there are preferred alkali metal or alkaline earth metal salts of bile acids and of their conjugates. Advantageous concentrations of anionic detergents are from about 2 to about 10 mmole/liter. Sodium cholate in concentrations of from about 4 to about 6 mmole/liter have proved to be especially favourable.

Cationic detergents as, for example oxyethylalkylammonium phosphate (for example, Dehyquart®SP, Henkel, West Germany) are used in concentrations from about 0.5 to about 4% by volume. A preferred range of concentration for such detergents has been determined to be from about 1 to about 2% by volume.

As non-ionic detergents, a broad palette of detergents is available for choice. Preferable nonionic detergents include, above all, linear or branched-chain alkyl or alkylaryl alcohol-polyglycol ethers with 8 to 20 carbon atoms in the alcohol moiety and with 4 to 15 glycol units per molecule. An especially advantageous activating action is exerted by linear and branched-chained alkyl alcohol-polyglycol ethers with 8 to 12 carbon atoms in the alcohol moiety and with 4 to 8 glycol units per molecule.

For the process according to the present invention for the specific determination of the serum fructosamine content, non-ionic detergents can be used which, with regard to the structure of the alcohol of the alcohol moiety, can be uniform or can be a mixture of several polyglycol ethers differing with regard to the structure of the alcohol moiety. Especially preferred is a mixture of an isodecanol polyglycol ether with an average of four glycol units per molecule, for example, (Oxetal) ® ID 104 of the firm Zschimmer & Schwarz, Lahnstein, West Germany) and an n-decanol polyglycol ether with an average of 6 glycol units per molecule, for example, (Product RT 240 ®) of the firm Zschimmer & Schwarz, Lahnstein, West Germany). The concentration of non-ionic detergent which, according to the present invention, is added for the removal of non-specific reducing-acting and/or turbidity-causing sample components can be from 0.05 to 15% by weight. The preferred concentration range of Oxetal ® ID 104 was proved to be 0.1 to 1% and especially advantageously from 0.2 to 0.5%. Product RT 240 ® can be used in a concentration of from 1 to 10% and especially preferably of from 2 to 5%.

The turbidity-removing action can be further improved by higher ionic strengths in the reaction solution. For this purpose, there have proved to be favourable additions of salts of mineral acids which also remain in solution in the alkaline pH range. Alkali metal and alkaline earth metal salts of hydrochloric or sulphuric acid are preferred and potassium or sodium chloride are especially preferably added. The concentration of the added salts of mineral acids can be from 20 to 100 mmole/liter. Especially preferably, these salts are added in the concentration of from 40 to 60 mmole/liter.

The removal of non-specific reducing-acting and/or turbidity-causing sample components takes place at a temperature of from 25° to 40° C. and preferably of about 37° C. over a time period of from 1 to 15 minutes and preferably of from 2 to 6 minutes. The time period for the incubation to be chosen is dependent upon the amount of non-specific reducing-acting and turbidity-causing sample components and upon the amount of enzymatic or/and non-enzymatic oxidizing agents used for the removal thereof.

Since the incubation for the removal of non-specific reducing-acting and/or turbidity-causing sample components is, because of the pH optimum of the enzymes used, carried out at approximately neutral pH value but the colour reaction between colour reagent and fructosamine takes place at a pH value of from about 10 to about 12, it is necessary to rebuffer after incubation has taken place. The increasing of the pH value takes place by means of a buffer, the pH value of which lies somewhat above the pH value to be adjusted. A buffer with a pH value of from about 10.5 to about 12.5 and especially preferably of from about 10.7 to about 12.2, is especially expedient. For this purpose, there is advantageously used a carbonate buffer, the concentration of which can be from 150 to 300 mmole/liter and especially preferably from 180 to 220 mmole/liter.

By the addition of a colour reagent in the alkaline range, the reducing action of the fructosamine can be made visible in known manner. For this purpose, there is preferably used a tetrazolium salt, the coloured formazane formation of which can be monitored visually or photometrically. As tetrazolium salts, those are preferred which are described in "Methods of Enzymatic Analysis" (H. U. Bergmeyer, ed., 3rd edition, pub. Verlag Chemie Weinheim, 1983, Volume I, page 200). Especially preferred are nitrotetrazolium blue (NBT) or 3-(4',5'-dimethylthiazolyl-2-)-2,4-diphenyl-tetrazolium-bromide (MTT). The colour reagent can be added to the test batch not only after the rebuffering but also simultaneously with the buffer. For this purpose, it has proved to be advantageous to dissolve the colour reagent in the buffer needed for the rebuffering. For tetrazolium salts, concentrations of from 0.2 to 2 mmole/liter have proved to be favourable and of from 0.4 to 1.5 mmole/liter especially favourable.

For the rebuffering after the removal of non-specific reducing-acting and/or turbidity-causing sample components, so much buffer is added that the pH value of the test batch in the presence of the colour reagent has a pH value of from 10 to 12 and preferably of from 10.3 to 10.6.

The rebuffered solution is incubated at a temperature of from 25° to 40° C. and preferably of about 37° C. The colour change depending upon the reduction of the colour reagent is monitored photometrically for a definite period of time and preferably for 1 to 15 minutes after rebuffering has taken place. A first measurement is carried out 1 to 10 minutes after the rebuffering and a last measurement 2 to 15 minutes after the rebuffering. Depending upon requirements, two or more measurements can be carried out. The time intervals between two measurements are variable. They can be chosen according to the apparatus used and can be from a few seconds to a few minutes.

In some cases, it is desirable to compare the measurement values obtained with those of a standard solution. Appropriate standard solutions are known. For example, for this purpose, there can be used the standard described by Johnson et al. in Clin. Chim. Acta, 127, 87–95/1982, which is based on a matrix of human albumin with known additions of a synthetic fructosamine. As synthetic fructosamine, there is used 1-desoxy-1-morpholinofructose (DMF). The determined serum fructosamine concentration in the sample is, when using this standard, given in DMF units.

Surprisingly, the process according to the present invention also permits the sample/reagent volume ratio to be considerably reduced from 0.1, which is usual according to the process of Johnson et al., without, in the case of the same measurement interval and incubation at the same temperature, the measurement signal with a definite amount of fructosamine analogue used as sample becoming significantly smaller in comparison with the method described by Johnson et al. If, as fructosamine analogue, there is used, for example, DMF, then, in this case, the sample/reagent volume ratio can be reduced to 0.02 without reducing the sensitivity of the measurement.

The process according to the present invention for the determination of fructosamine in blood or samples derived from blood, whereby non-specific reducing-acting and/or turbidity-causing sample components are removed with the help of one or more enzymatic or-/and non-enzymatic oxidizing agents, as well as optionally one or more detergents and/or salts, can be carried out not only in solution but also with the use of dry chemical test carriers. For this purpose, the oxidizing agent or oxidizing agents, as well as optionally one or more detergents and/or salts and optionally with further adjuvant materials, are applied in known manner to solid carriers. Appropriate solid carriers, as well as processes for the application of these materials or material mixtures to such carriers, are well known. As carrier materials, there can be used, for example, all possible absorbent materials, such as papers, fleece and the like. The materials to be applied can be taken up in one or more impregnation solutions. The carriers are impregnated or sprayed with these solutions and subsequently dried.

Another possibility is to introduce the oxidizing agent or oxidizing agents, as well as optionally detergents and/or salts and also optionally further adjuvant materials, into reagent films. For this purpose, the substances or substance mixtures are worked up to give reagent films, for example according to the processes described in U.S. Pat. Nos. 3,630,957 and 4,312,834.

For the removal of disturbing non-specific reducing-acting and/or turbidity-causing sample components, the sample to be measured is first brought into contact with a carrier which contains the oxidizing agent or oxidizing agents, as well as optionally one or more detergents and/or salts. After sufficient contact, the pre-treated sample is transferred into a layer which contains the further reaction components necessary for the colour reaction. The colour change thereby brought about is measured in known manner photometrically, for example reflectometrically. With regard to the time interval for the pre-reaction and for the colour reaction, the statements made above also apply.

The present invention also provides a reagent mixture for the specific determination of serum fructosamine content in blood or samples derived from blood, wherein it comprises a reagent for the removal of non-specific reducing-acting and/or turbidity-causing sample components, a rebuffering reagent with a buffer which has a pH value in the range of from 10.5 to 12.5 and a colour reagent for the detection of the fructosamine. This reagent mixture contains all the components necessary for carrying out the process according to the present invention.

The reagent for the removal of non-specific reducing-acting and/or turbidity-causing sample components in blood or samples derived from blood comprises one or more enzymatic and/or non-enzymatic oxidizing agents, as well as optionally peroxidase and/or catalase and/or lipase, as well as optionally one or more detergents and/or salts of mineral acids, and also optionally conventional additive materials, in a buffer with an approximately neutral pH value.

By enzymatic oxidizing agents are to be understood, in particular, ascorbate oxidase, bilirubin oxidase and uricase and by non-enzymatic oxidizing agents are to be understood, in particular, hypochlorite or hypochlorite generating compounds.

The detergents contained in the reagent according to the present invention for the removal of non-specific reducing-acting and/or turbidity-causing sample components in blood or samples derived from blood can be anionic or non-ionic. Whereas, as anionic detergents, in particular there are preferred alkali metal and alkaline earth metal salts of bile acids and of their conjugates, for the non-ionic detergents there is a broad palette of detergents for selection. As appropriate, there have proved to be, above all, linear or branched-chain alkyl or alkylaryl alcohol-polyglycol ethers with 8-20 carbon atoms in the alcohol moiety and with 4 to 15 glycol units per molecule. The added detergents additionally can be cationic detergents, for example oxyethylalkylammoniumphosphate (for example Dehyquart ®SP). Especially potent is a mixture of enzymatic or/and non-enzymatic oxidizing agents, if it comprises chlormaine T and additionally a cationic detergent, for example oxyethylalkylammoniumphosphate (for example Dehyquart ®SP).

As salts of mineral acids, for the reagent according to the present invention, alkali metal and alkaline earth metal salts of hydrochloric or sulphuric acid have proved to be preferable, potassium and sodium chloride being especially preferred.

The buffer necessary for the achievement of a substantially neutral pH value of the reagent according to the present invention has a pH value in the range of from 6 to 9, preferably of from 7 to 8.5 and especially preferably of from 7.5 to 8.0. The buffer concentration is preferably from 10 to 100 mmole/liter and especially preferably from 20 to 70 mmole/liter. Aqueous potassium phosphate buffer has proved to be especially advantageous.

The following Examples are given for the purpose of illustrating the present invention:

EXAMPLE 1

Fructosamine determination

A) Reagent composition

| components | concentration |
| --- | --- |
| a) Reagent I (for the first incubation step) | |
| potassium phosphate buffer (pH 8.0) | 50 mmole/l. |
| potassium chloride | 50 mmole/l. |
| sodium cholate | 5 mmole/l. |
| Oxetal ® ID 104 | 0.25% |
| Product RT 240 ® | 3% |
| uricase | 4 U/ml. |
| bilirubin oxidase | 0.1 U/ml. |
| lipase | 2 U/ml. |
| ascorbate oxidase | 10 U/ml. |
| peroxidase | 2 U/ml. |
| catalase | 1000 U/ml. |
| b) Reagent II (for the second incubation step) | |
| sodium carbonate buffer (pH 10.9) | 200 mmole/l. |
| nitro blue tetrazolium salt | 0.5 mmole/l. |

B) Test carrying out

Wavelength: 546 nm
temperature: 37° C.
layer thickness: 10 mm. (semimicrocuvette)
Into cuvettes pipette:

| | sample (P) | reagent blank (RL) |
| --- | --- | --- |
| Reagent I | 0.500 ml. | 0.500 ml. |
| sample | 0.020 ml. | — |
| distilled water | — | 0.020 ml. | incubate 5 minutes, subsequently admix:

| Reagent II | 0.500 ml. | 0.500 ml. |
| --- | --- | --- | again incubate and measure the kinetics of the coloured material formation ($\Delta E_p$ or $\Delta E_{RL}$) within a definite time interval $\Delta t$ (1 to 15 minutes) after the addition of Reagent II.

$$\Delta E = (\Delta E_P - \Delta E_{RL})/\Delta t$$

In corresponding way as carried out above for the sample, there is measured a standard solution (S) with known DMF content. From the measurement values, there is determined $\Delta E_{standard}$ in the following way:

$$\Delta E_{standard} = (\Delta E_S - \Delta E_{RL})/\Delta t$$

$$\text{Concentration in the sample} = \frac{\Delta E}{\Delta E_{standard}}$$

The concentration in the sample is given in "1-desoxymorpholinofructose units" (DMF units). For the calibration, there is used the calibration standard from the fructosamine test of the firm Roche, Basel, Switzerland (article No. 07-1121-7).

Figure 1:
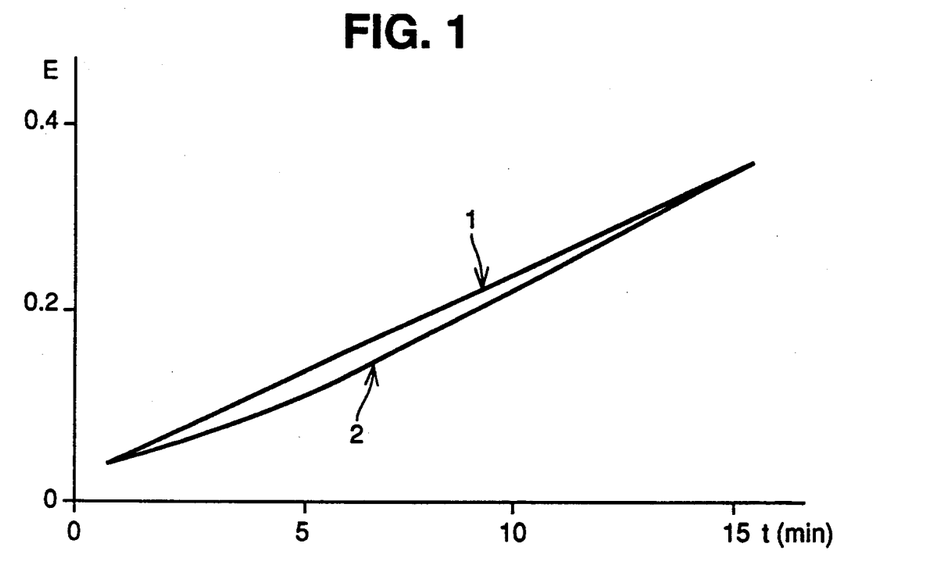
FIG. 1 shows a comparison of the process following the invention as compared to the prior art.

An illustration of the course of the extinction in the case of the test batch with the process according to the present invention (curve 1) in comparison with the method of Johnson et al., Clin. Chim. Acta, 127, 87-95/1982 (curve 2) whereby the calibration standard from the fructosamine test of the firm Roche, Basel, Switzerland, serves as sample material, is given in FIG. 1 of the accompanying drawings.

EXAMPLE 2

Linearity

For testing the linearity of the extinction change in the process according to the present invention, a human serum is made up stepwise with 1-deoxy-1-morpholino-fructose (DMF) and the test is carried out according to Example 1.

Figure 2:
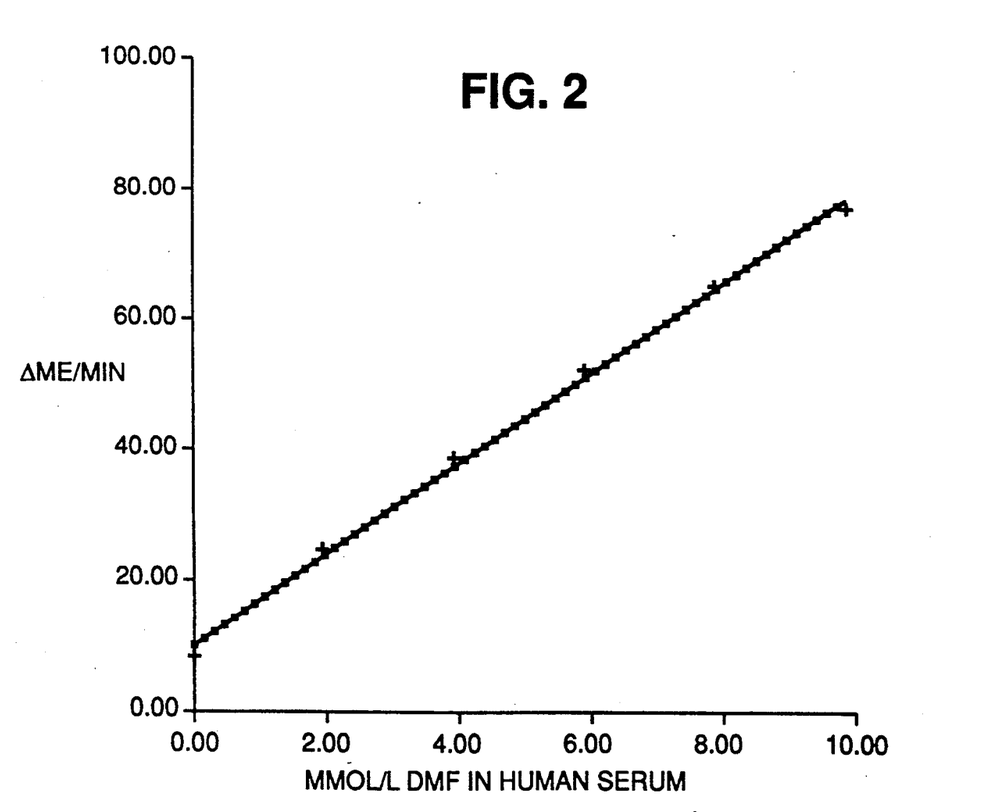
FIG. 2 shows the linearity of the process in accordance with the invention, graphing $\Delta E$/minute against analyte concentration.

As can be seen from FIG. 2 of the accompanying drawings, the extinction change/minute up to at least 10 mmole/liter is linearly proportional to the DMF concentration of the sample.

EXAMPLE 3

Bilirubin disturbance

For the investigation of the influence of bilirubin on the measurement signal in the process according to the present invention for the determination of fructosamine, a human serum is made up stepwise with bilirubin up to a concentration of 12 mg./dl. and the test is carried out as described in Example 1.

Figure 3:
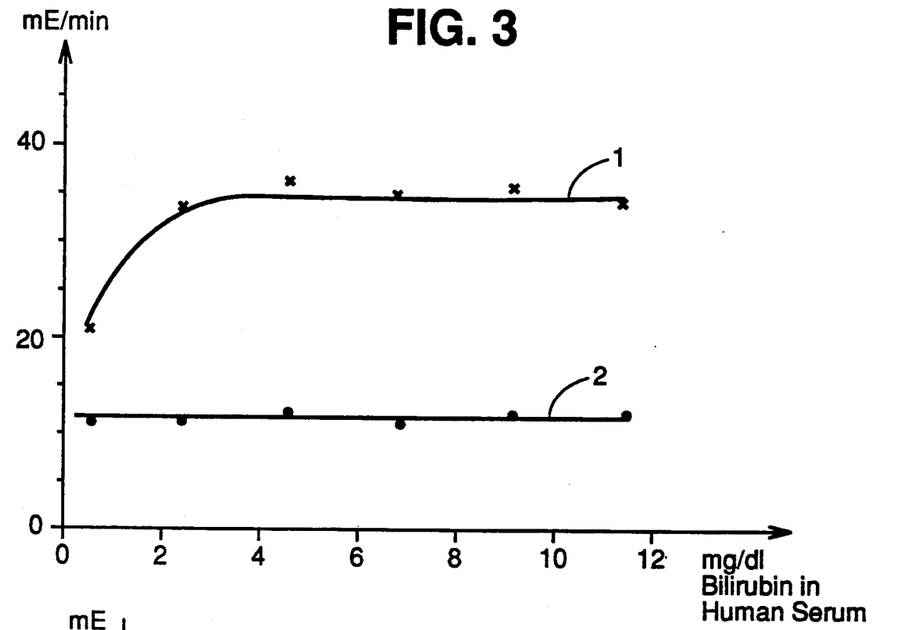
FIG. 3 compares bilirubin influence using the invention and the prior art.

As is to be seen from FIG. 3 of the accompanying drawings, in the case of the frustosamine determination according to the process of Johnson et al., Clin. Chim. Acta, 127, 87-95/1982 (curve 1), even a bilirubin concentration of 2 mg./dl. leads to a measurement signal increased by about 40%, whereas in the test process according to the present invention (curve 2), with up to at least 2 mg./dl. it remains completely uninfluenced.

EXAMPLE 4

Uric acid disturbance

For the determination of the influence of uric acid on the measurement signal, human serum is made up with various amounts of uric acid and an E/t diagram made, on the one hand, according to the process of Johnson et al., Clin. Chim. Acta, 127, 87-95/1982, and, on the other hand, according to the method according to the present invention, analogously to Example 1.

| | | ΔE/5 min. (% finding again) | |
|---|---|---|---|
| sample | uric acid (mg./dl.) | method according to Johnson et al. | method according to the present invention |
| 1 | 6.9 | 0.082 (100%) | 0.081 (100%) |
| 2 | 13.7 | 0.093 (113%) | 0.082 (101%) |
| 3 | 17.8 | 0.097 (118%) | 0.080 (99%) |
| 4 | 24.2 | 0.104 (127%) | 0.081 (100%) |
| 5 | 30.0 | 0.107 (130%) | 0.083 (102%) |

Whereas in the test according to Johnson et al., even in the case of a uric acid concentration of 13.7 mg./dl., there is found, in comparison with the starting value (6.9 mg. uric acid/dl.), a signal increased by 13%, the test with the process according to the present invention remains practically uninfluenced by uric acid up to concentrations of about 30 mg./dl.

EXAMPLE 5

Ascorbic acid disturbance

For the determination of the influence of ascorbic acid on the measurement signal, human serum is made up with various amounts of ascorbic acid and an E/t diagram made, on the one hand according to the process of Johnson et al., Clin. Chim. Acta, 127, 87-96/1982, and, on the other hand, with the method according to the present invention, analogously to Example 1.

| | | ΔΔ (% finding again) | |
|---|---|---|---|
| sample | ascorbic acid (mg./l.) | method according to Johnson et al. | method according to the present invention |
| 1 | 0 | 16.2 (100%) | 16.5 (100%) |
| 2 | 10 | 15.6 (96.3) | 16.5 (100%) |
| 3 | 20 | 15.4 (95.1) | 17.0 (103%) |
| 4 | 30 | 14.8 (91.7) | 17.5 (106%) |
| 5 | 50 | 14.2 (87.7) | 17.0 (103%) |

Whereas in the case of the test according to Johnson et al., with increasing ascorbic acid concentration, the finding again rate decreases increasingly, the test with the process according to the present invention remains practically uninfluenced up to concentrations of about 50 mg./l.

EXAMPLE 6

Clarification of lipaemic sera

In a test batch corresponding to Example 1, as sample there is used a strongly hyperlipaemic serum (triglycerides, 2000 mg./dl.).

Figure 4:
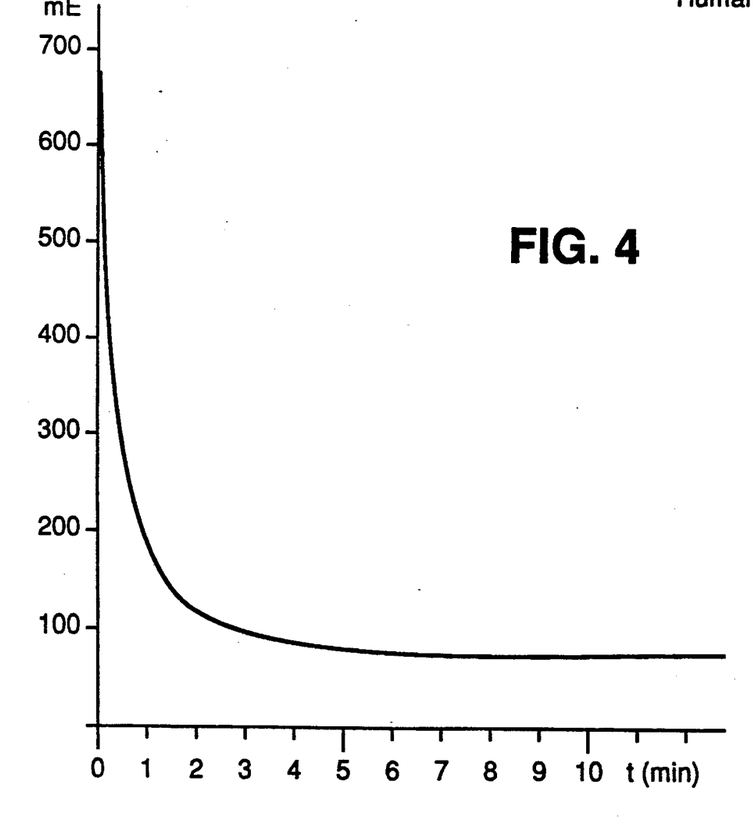
FIG. 4 shows the efficacy of the invention in eliminating sample turbidity.

As can be seen from FIG. 4 of the accompanying drawings, in the first incubation step, even after 5 minutes, a complete and long-lasting turbidity removal is achieved.

EXAMPLE 7

Medicament disturbance

For the determination of the influence of medicaments on the measurement signal, human serum is made up with various amounts of different medicaments or medicament metabolic products and an E/t diagram made according to the process of Johnson et al., Clin. Chim. Acta, 127, 87-95/1982, as well as with the process according to the present invention, analogously to Example 1.

| medicament or breakdown product | concentration in the serum | ΔmE/min. (% finding again) | |
|---|---|---|---|
| | | test according to Johnson et al. | test according to the present invention |
| α-methyl-dopa | 0 | 17.4 (100%) | 15.6 (100%) |
| | 1 mg./l. | 18.4 (106%) | 16.1 (103%) |
| | 10 mg./l. | 22.6 (130%) | 17.2 (110%) |
| | 100 mg./l. | no longer measurable | 22.5 (144%) |
| gentisic acid Na salt | 0 | 17.4 (100%) | 15.6 (100%) |
| | 1 mg./l. | 19.2 (110%) | 15.9 (102%) |
| | 10 mg./l. | 24.8 (143%) | 16.7 (107%) |
| | 100 mg./l. | about 390 (2000%) | 22.2 (142%) |

EXAMPLE 8

Influence of the sample total protein amount on the measurement signal

In a model experiment, solutions are prepared with various concentrations of bovine serum albumin (BSA) in physiological saline, on the one hand, without the addition of 1-deoxymorpholinofructose (DMF) for a blank value determination and, on the other hand, with the addition of a constant amount of DMF (2.5 mmol/l.). The test was carried out not only according to the method of Johnson et al., Clin. Chim. Acta, 127, 87-95/1982, but also according to the process of the present invention according to Example 1.

|  | ΔmE/min. | |
| --- | --- | --- |
|  | test according to Johnson et al. | test according to the process according to the present invention |
| BSA without DMF (g./l.) | | |
| 0 | 0.0 | 2.8 |
| 20 | 12.1 | 4.9 |
| 40 | 17.8 | 7.0 |
| 60 | 18.7 | 8.3 |
| 80 | 21.9 | 9.4 |
| 100 | 23.8 | 10.8 |
| BSA with DMF | difference: (ΔmE/min.) with DMF − (ΔmE min. without DMF (% finding again) | |
| 0 | 15.9 (100%) | 12.3 (100%) |
| 20 | 11.1 (70%) | 12.1 (98%) |
| 40 | 9.8 (62%) | 12.2 (99%) |
| 60 | 8.8 (55%) | 11.2 (91%) |
| 80 | 6.2 (39%) | 11.1 (90%) |
| 100 | 4.3 (27%) | 12.0 (97%) |

As is to be seen from the above Table, the measurement produced by DMF in the sample in the test according to Johnson et al. is, in the case of increasing protein concentrations, very strongly reduced, whereas in the test according to the process of the present invention, up to at least 100 g. BSA/liter, it is practically uninfluenced by the amount of protein.

EXAMPLE 9

Fructosamine determination

A) Reagent composition

| components | concentration |
| --- | --- |
| a) Reagent I (for the first incubation step) | |
| potassium phosphate buffer (pH 8.0) | 50 mmole/l. |
| potassium chloride | 50 mmole/l. |
| sodium cholate | 7 mmole/l. |
| Lutensol ® ON6O (BASF) | 2.4% |
| uricase | 4 U/ml. |
| bilirubin oxidase | 0.1 U/ml. |
| lipase | 2 U/ml. |
| ascorbate oxidase | 10 U/ml. |
| peroxidase | 2 U/ml. |
| b) Reagent II (for the second incubation step) | |
| sodium carbonate buffer (pH 10.9) | 200 mmole/l. |
| nitro blue tetrazolium salt | 0.5 mmole/l. |

B) Test carrying out

The tests were carried out on a Hitachi 704 automatic analyzer.
Wavelength: 546 nm
temperature: 37° C.
layer thickness: 10 mm. (semimicrocuvette)
Into cuvettes pipette:

|  | sample (P) | reagent blank (RL) |
| --- | --- | --- |
| Reagent I | 0.175 ml. | 0.175 ml. |
| sample | 0.007 ml. | — |
| distilled water | — | 0.007 ml. | incubate 5 minutes, subsequently admix:

| | sample (P) | reagent blank (RL) |
| --- | --- | --- |
| Reagent II | 0.175 ml. | 0.175 ml. | again incubate and measure the kinetics of the coloured material formation ($\Delta E_p$ or $\Delta E_{RL}$) within a definite time interval $\Delta t$ (8 to 10 minutes) after the addition of Reagent III.

Figure 5A:
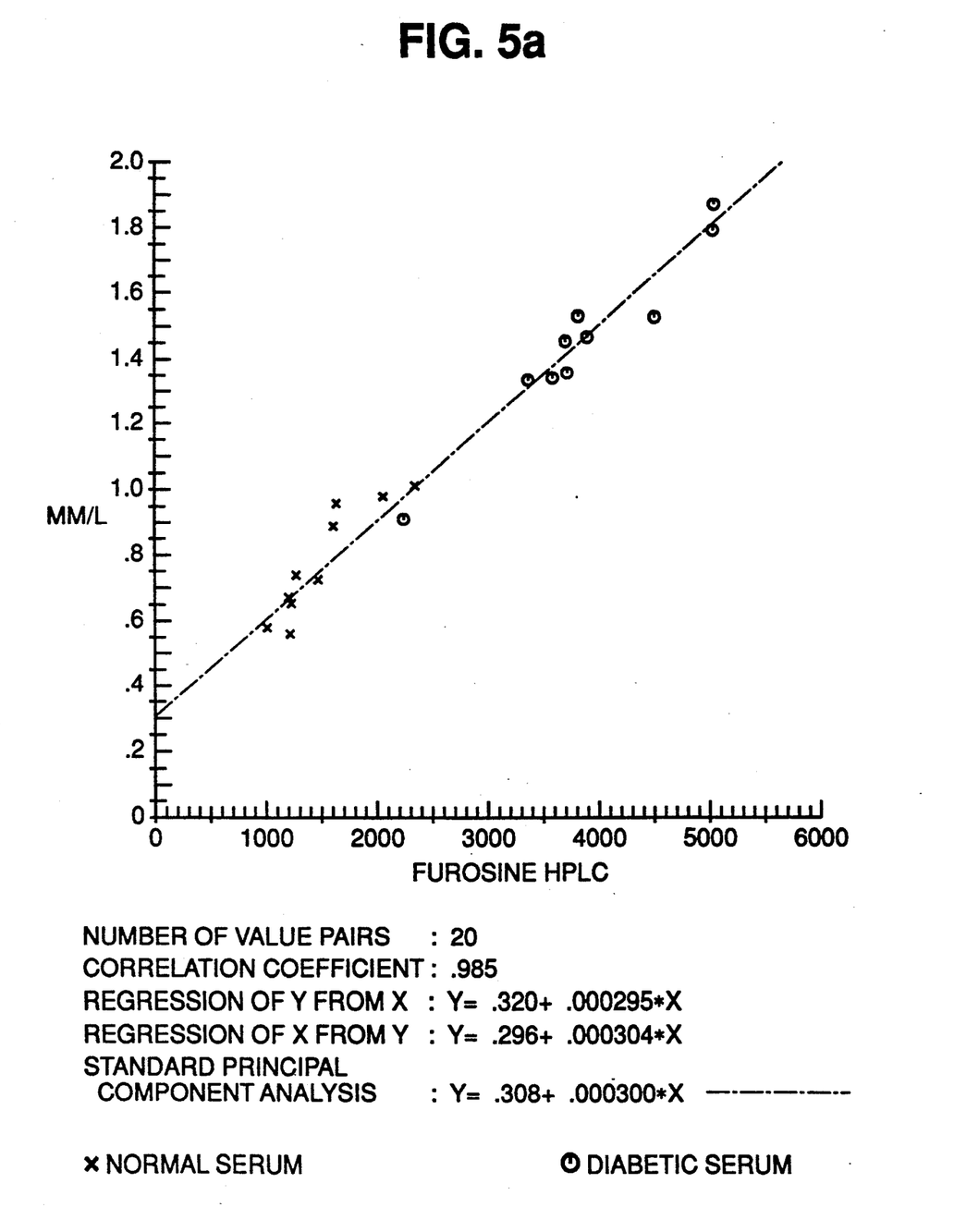
FIGS. 5a–5d depict the invention when being used in combination with various reagents.

The concentrations of fructosamine were determined by analogy to example 1 as DMF-units and were plotted in mM (mmol/L) on the ordinate of FIG. 5a. These results were plotted against the measured values obtained for furosine by the HPLC-reference-method (J. Clin. Chem. Clin. Biochem. 19 (1981), page 81 to 87).

As HPLC-measured values the corresponding relative peak area units were used.

Figure 5B:
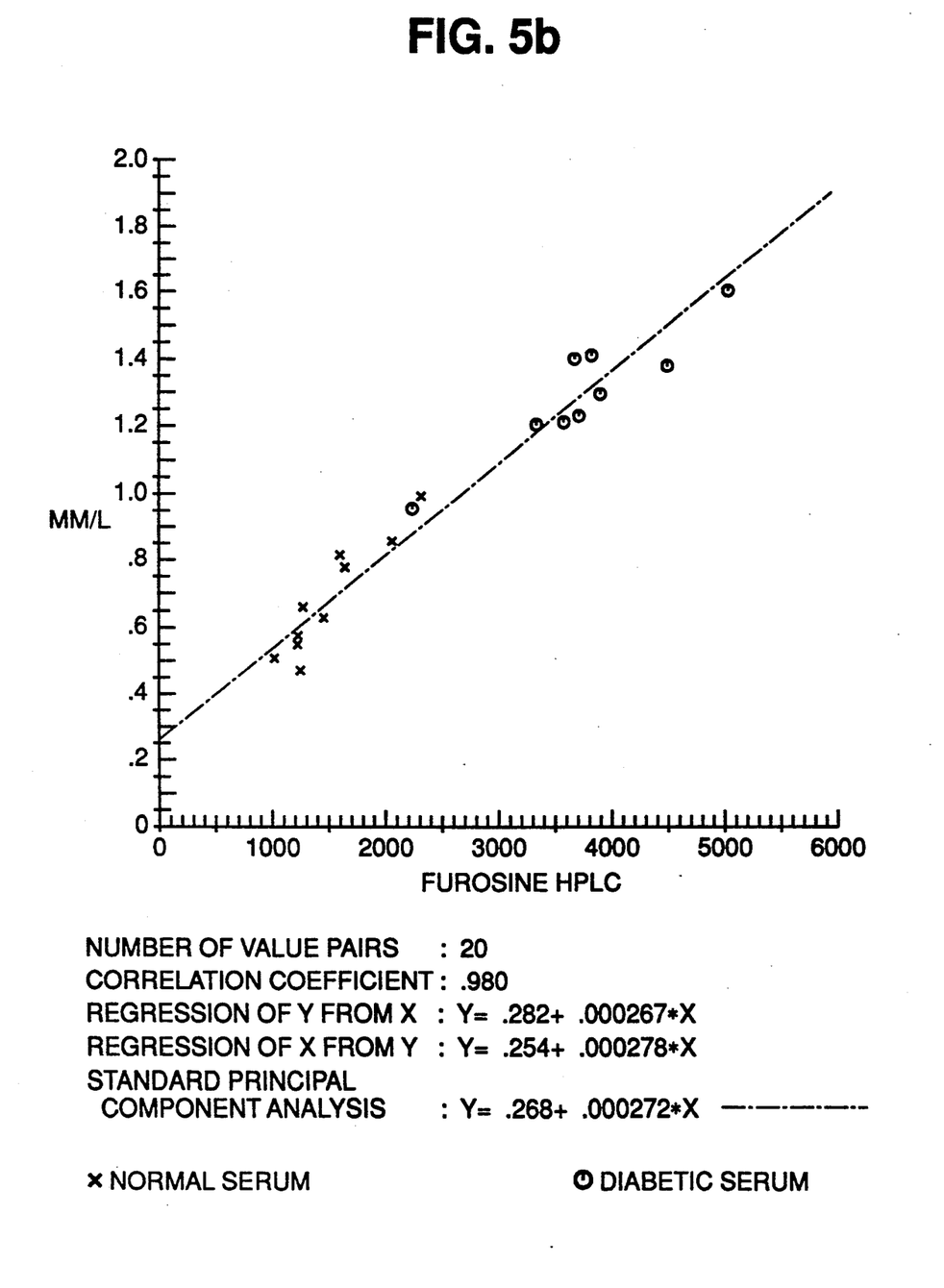

In FIG. 5b the results are plotted for an analogous determination of fructosamine, the Reagent I additionally containing 1.2% by weight Dehyquart ®SP (of the firm Henkel).

Figure 5C:
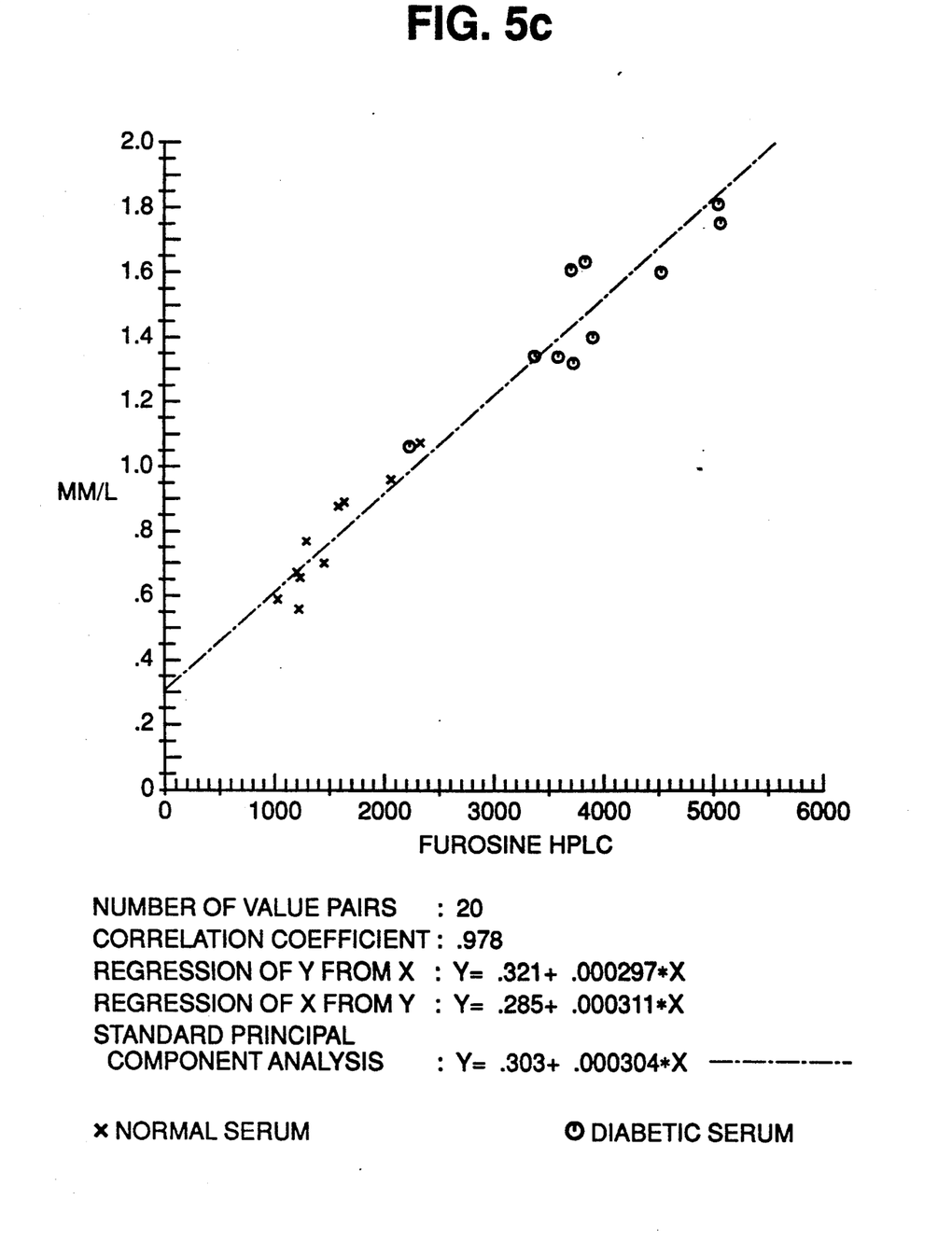

FIG. 5c shows the measurement results of an analogous determination of fructosamine, the Reagent I additionally containing 250 µM Chloramine T.

Figure 5D:
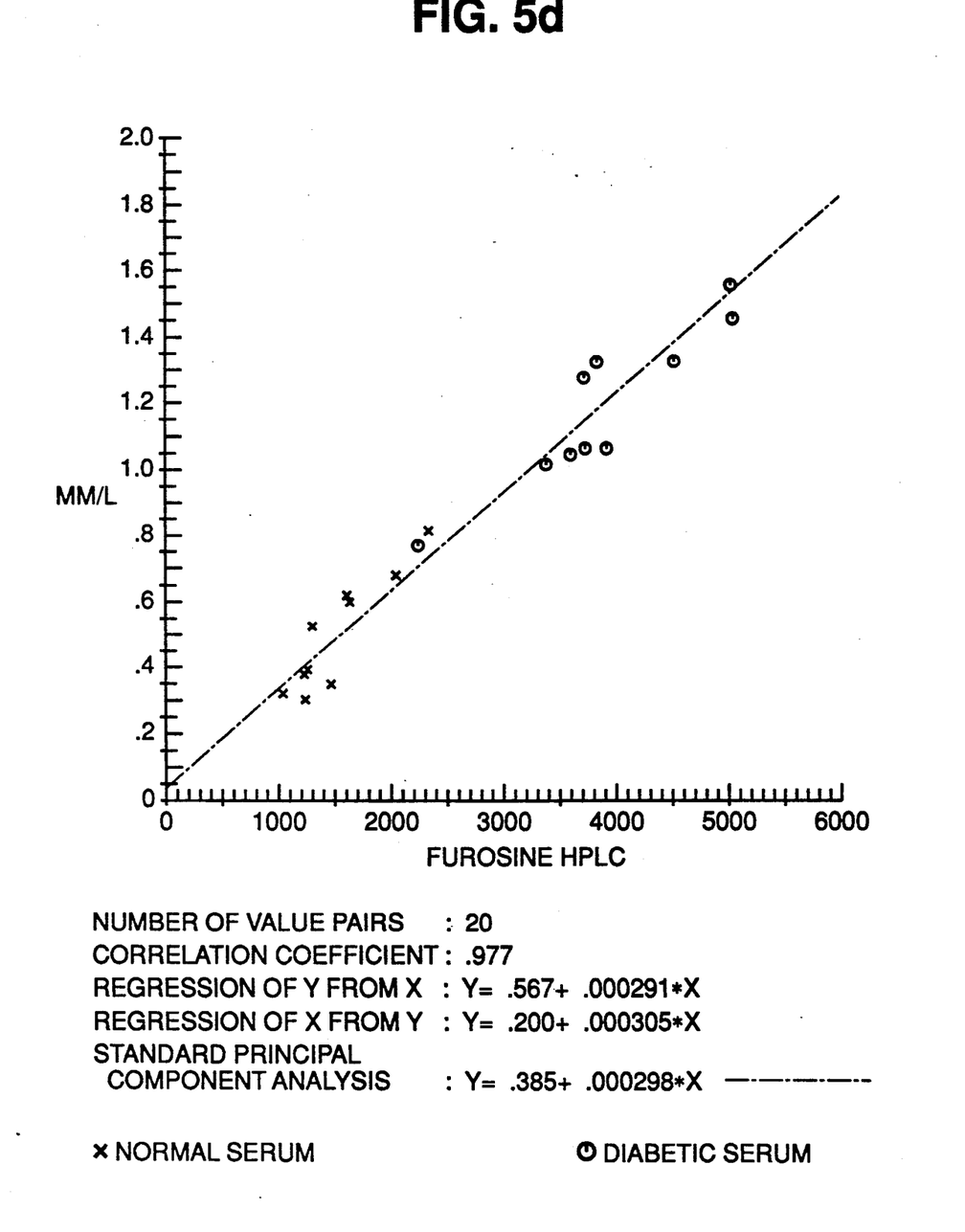

FIG. 5d shows the measurement results of an analogous determination of fructosamine, the Reagent I additionally containing 1.2% by weight Dehyquart ®SP as well as 250 µM Chloramine T.

From the diagrams 5a–d is to be learned that especially the combination of Chloramine T and Dehyquart ®SP obviously reduces the axial section.

While there have been described what are at present considered to be the preferred embodiments of this invention, it will be obvious to one skilled in the art that various changes and modifications may be made therein without departing from the invention, and it is, therefore, aimed to cover all such changes and modifications as fall within the true spirit and scope of the invention.

We claim:

1. Process for the reduction of any protein matrix effects in an assay for specific determination of serum fructosamine in a blood sample or sample derived from blood, comprising: (i) adding to said sample a first, peroxidase containing reagent which eliminates any non-specific reducing agents present in said sample which reduce and interfere with a reagent which reacts with fructosamine to form a color change, and a second reagent which eliminates any turbidity causing substances in said sample, said first and second reagents being added in an amount sufficient to reduce any matrix effects in said sample, (ii) incubating said sample and reagents to remove any non-specific reducing agents and turbidity causing substances from said sample, (iii) adjusting the pH of said sample to a pH of from about 10 to about 12, and (iv) adding a color reagent to said sample which reacts with serum fructosamine present in said sample to form a color change if fructosamine is present, and measuring any color change as a determination of serum fructosamine in said sample.

2. Process of claim 1 wherein said first, peroxidase containing reagent comprises at least one oxidizing agent which removes any non-specific reducing substances which reduce and interfere with the color reagent which reacts with fructosamine to form a color change.

3. Process according to claim 2, wherein said at least one oxidizing agent is an enzymatic oxidizing agent.

4. Process of claim 3, wherein said enzymatic oxidizing agent is selected from the group consisting of ascorbate oxidase, bilirubin oxidase, and uricase.

5. Process of claim 2, wherein said at least one oxidizing agent is a non-enzymatic oxidizing agent.

6. Process of claim 5, wherein said first, peroxidase containing reagent further comprises a cationic detergent.

7. Process of claim 6, wherein said cationic detergent is oxyethylammonium phosphate.

8. Process of claim 1, wherein said first reagent further comprises catalase.

9. Process of claim 1, wherein said first reagent further comprises a non-enzymatic oxidizing agent selected from the group consisting of hypochlorite and a hypochlorite generating compound.

10. Process of claim 9, wherein said oxidizing agent comprises said hypochlorite generating compound which is N-chloro-p-toluene-sulfonamide.

11. Process of claim 9, comprising adding said hypochlorite or hypochlorite generating compound at a concentration of from about 50 to about 600 μmol/l.

12. Process of claim 11, comprising adding said hypochlorite or hypochlorite generating compound at a concentration of from about 150 to about 300 μmol/l.

13. Process of claim 1, wherein said second reagent comprises a lipase and a mineral acid salt.

14. Process of claim 13, wherein said second reagent further comprises a detergent.

15. Process of claim 14, wherein said detergent is an anionic or non-ionic detergent.

16. Process of claim 13, wherein said mineral acid salt is an alkali metal salt of hypochloric acid, an alkaline earth metal salt of hydrochloric acid, an alkali metal salt or sulphuric acid or an alkaline metal salt of sulphuric acid.

17. Process of claim 1 wherein said second reagent comprises a lipase.

18. Process of claim 1 wherein said second reagent further comprises a detergent.

19. Process for the reduction of any protein matrix effects in an assay for specific determination of serum fructosamine in a blood sample or sample derived blood, comprising: (i) adding to said sample a first catalase containing reagent which eliminates any non-specific reducing agents present in said sample which reduce and interfere with a reagent which reacts with fructosamine to form a color change, and a second reagent which eliminates any turbidity causing substances in said sample, said first and second reagents being added in an amount sufficient to reduce any matrix effects in said sample, (ii) incubating said sample and reagents to remove any non-specific reducing agents and turbidity causing substances from said sample, (iii) adjusting the pH of said sample to a pH of from about 10 to about 12, and (iv) adding a color reagent to said sample which reacts with serum fructosamine present in said sample to form a color change if fructosamine is present, and measuring any color change as a determination of serum fructosamine in said sample.

20. Process for the reduction of any protein matrix effects in an assay for specific determination of serum fructosamine in a blood sample or sample derived from blood, comprising: (i) adding to said sample a first, oxidizing, agent containing reagent wherein said oxidizing agent comprises a compound selected from the group consisting of hypochlorite and a hypochlorite generating compound which eliminates any non-specific reducing agents present in said sample which reduce and interfere with a reagent which reacts with fructosamine to form a color change, and a second reagent which eliminates any turbidity causing substances in said sample, said first and second reagents being added in an amount sufficient to reduce any matrix effects in said sample, (ii) incubating said sample and reagents to remove any non-specific reducing agents and turbidity causing substances from said sample, (iii) adjusting the pH of said sample to a pH of from about 10 to about 12, and (iv) adding a color reagent to said sample which reacts with serum fructosamine present in said sample to form a color change if fructosamine is present, and measuring any color change as a determination of serum fructosamine in said sample.

21. Process of claim 20, wherein said oxidizing agent comprises said hyprochlorite generating compound which is N-chloro-p-toluene-sulfonamide.

22. Process of claim 20, further comprising adding a lipase to said sample.

23. Process of claim 22, further comprising adding a detergent to said sample.

24. Process for the reduction of any protein matrix effects in an assay for specific determination of serum fructosamine in a blood sample derived from blood, comprising: (i) adding to said sample a first reagent which eliminates any non-specific reducing agents present in said sample which reduce and interfere with a reagent which reacts with fructosamine to form a color change, a second reagent which eliminates any turbidity causing substances in said sample, said first and second reagents being added in an amount sufficient to reduce any matrix effects in said sample, a lipase, and a mineral acid salt, (ii) incubating said sample, reagents, lipase, and mineral acid salt to remove any non-specific reducing agents and turbidity causing substances from said sample, (iii) adjusting the pH of said sample to a pH of from about 10 to about 12, and (iv) adding a color reagent to said sample which reacts with serum fructosamine present in said sample to form a color change if fructosamine is present, and measuring any color change as a determination of serum fructosamine in said sample.

25. Process of claim 24 wherein said first reagent further comprises a detergent.

26. Process of claim 25, wherein said detergent is an anionic or non-ionic detergent.

27. Process of claim 24 wherein said mineral acid salt is an alkali metal salt of hydrochloric acid, an alkaline earth metal salt of hydrochloric acid, an alkali metal salt of sulphuric acid, or an alkaline earth metal salt of sulphuric acid.

28. Process of claim 24, wherein said first agent comprises at least one oxidizing agent which removes any non-specific reducing substances which reduce and interfere with the color reagent which reacts with fructosamine to form a color change.

29. Process of claim 28, wherein said at least one oxidizing agent is an enzymatic oxidizing agent.

30. Process of claim 28, wherein said at least one oxidizing agent is a non-enzymatic oxidizing agent.

31. Process of claim 30, wherein said non-enzymatic oxidizing agent is selected from the group consisting of hypochlorite and a hypochlorite generating compound.

* * * * *